United States Patent [19]

Cleveland et al.

[11] Patent Number: 5,090,797
[45] Date of Patent: Feb. 25, 1992

[54] METHOD AND APPARATUS FOR MIRROR CONTROL

[75] Inventors: Dixon Cleveland, Vienna; James H. Cleveland, Clifton; Peter L. Norloff, Fairfax, all of Va.; Jeffrey A. Forsythe, West Chester, Pa.; Richard W. Collier, Burke, Va.

[73] Assignee: LC Technologies Inc., Fairfax, Va.

[21] Appl. No.: 363,862

[22] Filed: Jun. 9, 1989

[51] Int. Cl.⁵ .......................... A61B 3/14; G02B 5/08
[52] U.S. Cl. ..................................... 351/210; 359/872
[58] Field of Search ............... 351/208, 209, 210, 245, 351/246; 350/631, 632, 633, 634, 635, 636, 637; 250/203 R, 203.1–203.7

[56] References Cited

U.S. PATENT DOCUMENTS

| | | |
|---|---|---|
| 3,804,496 | 4/1974 | Crane et al. |
| 3,864,030 | 2/1975 | Cornsweet |
| 3,869,694 | 3/1975 | Merchant et al. |
| 4,003,642 | 1/1977 | Vogeley |
| 4,059,348 | 11/1977 | Jernigan |
| 4,199,785 | 4/1980 | McCullough et al. |
| 4,231,066 | 10/1980 | Merchant |
| 4,251,139 | 2/1981 | Matsumura |
| 4,287,410 | 9/1981 | Crane et al. |
| 4,315,610 | 2/1982 | Malueg |
| 4,373,787 | 2/1983 | Crane et al. |
| 4,410,233 | 10/1983 | Gerhardt et al. |
| 4,544,246 | 10/1985 | Crane et al. |
| 4,570,060 | 2/1986 | Tsumura et al. ................ 250/203 R |
| 4,626,089 | 12/1986 | Takahashi et al. |
| 4,635,203 | 1/1987 | Merchant |
| 4,648,052 | 3/1987 | Friedman et al. |
| 4,673,264 | 6/1987 | Takahashi |
| 4,678,295 | 7/1987 | Fisher ................................ 350/634 |
| 4,678,297 | 7/1987 | Ishikawa et al. |
| 4,695,959 | 9/1987 | Lees et al. |
| 4,725,722 | 2/1988 | Maeda et al. |
| 4,755,045 | 7/1988 | Borah et al. |
| 4,756,613 | 7/1988 | Okashita |
| 4,782,474 | 11/1988 | Arai et al. |
| 4,789,235 | 12/1988 | Borah et al. |
| 4,811,619 | 3/1989 | Cutburth |

OTHER PUBLICATIONS

J. Merchant et al., "A Remote Oculometer Permitting Head Movement", Report No. AMRL-TR-73-69, Aerospace Medical Research Laboratory, Air Force Systems Command, Dayton, Ohio (Oct. 1973).

R. Razdan et al., "Eye Tracking for Man/Machine Interfaces", Sensors, pp. 39 42ff (Sep. 1988).

Primary Examiner—Rodney B. Bovernick
Attorney, Agent, or Firm—Kirkland & Ellis

[57] ABSTRACT

It is sometimes required to track randomly moving objects with precision and high speed. This invention pertains to a mirro rotation assembly that provides precise, high-speed pitch and yaw tracking by rotating a low-moment-of-inertia mirror rather than rotating a heavier double gimballed mirror assembly or the camera-lens assembly itself. By pivoting the mirror on a single bearing point and controlling the mirror surface pitch and yaw by driving two mirror tie points along circumferential paths around the bearing point, a low moment of inertia is obtained. The low moment of inertia together with mirror velocity rather than position control permits higher speed tracking while maintaining the required precision. The velocity control strategy minimizes image blur resulting from unpredicted object motions.

11 Claims, 6 Drawing Sheets

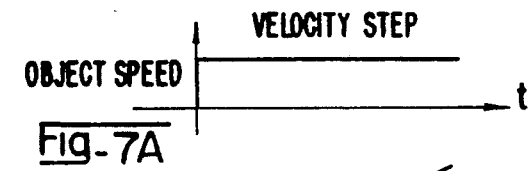
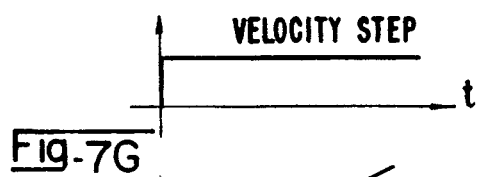
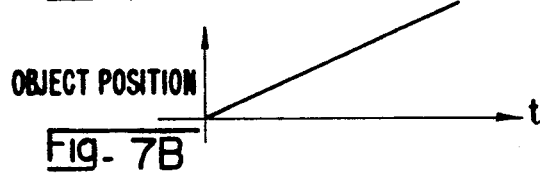
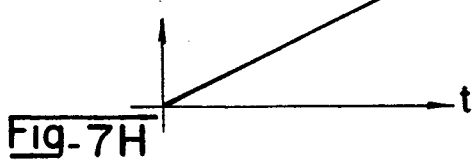
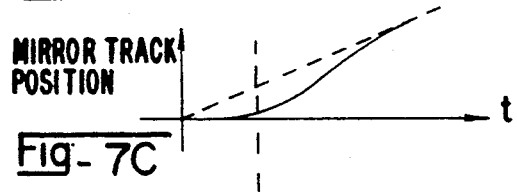
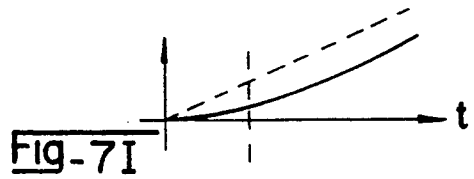
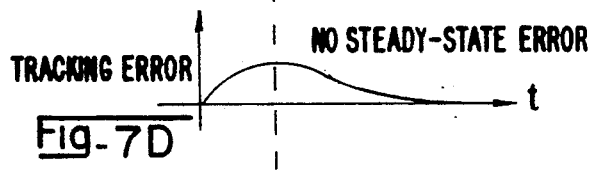
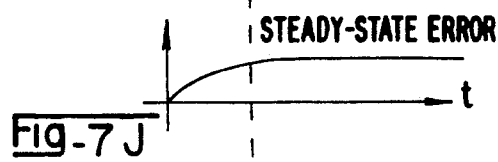
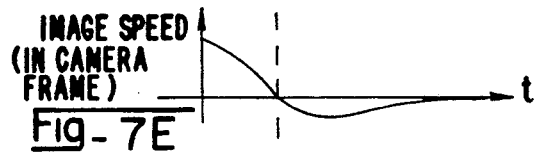
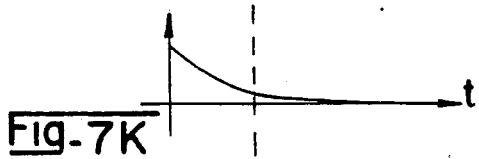
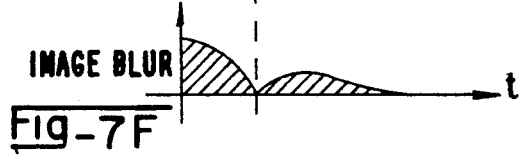
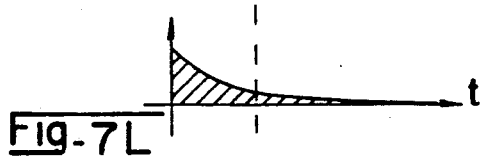
POSITION CONTROL STRATEGY
RATE CONTROL STRATEGY

METHOD AND APPARATUS FOR MIRROR CONTROL

BACKGROUND

The present invention relates to optical trackers and more particularly to a tracker for continuously tracking lateral movements of a person's eye.

This invention was conceived during the development of a system for tracking the pupil of a person's eye while both the head and eye are in motion. Prior eye-gaze trackers are disclosed in U.S. Pat. Nos. 3,864,030 to Cornsweet; 4,287,410 and 4,373,787 to Crane et al.; 4,648,052 to Friedman et al.; and in certain U.S. patent applications of Thomas E. Hutchinson, Ser. Nos. 07/086,809; 07/267,266, filed Nov. 3, 1988 now U.S. Pat. No. 4,836,670; and 07/326,787 now U.S. Pat. No. 4,973,143. Those systems typically illuminate the eye with infrared light which is reflected from various parts of the eye, particularly the cornea and pupil, to an imaging device such as a videocamera. The spatial relations between the corneal and pupil reflections are used to determine the gaze point. For example, the corneal reflection moves about eighty micrometers per degree of eye rotation with respect to the center of the pupil reflection.

It will be understood, however, that unless a corneal reflection tracker is head-mounted or the head restrained so that only in-socket eye rotations are detected, lateral motions of the head (and eye) can generate large errors, e.g., one degree for each eighth-millimeter, in the calculated gaze point. Sophisticated image processing can compensate for such lateral motions, but only to an extent limited by, among other factors, the instantaneous field of view of the camera. Since many potential users of eye-gaze trackers cannot completely control the positions of their heads, means are usually provided to move the field of view of the camera so as to track head motions.

To obtain clear, non-blurred images of an eye in high speed motion, the tracker must be capable of high angular accelerations and velocities. Because of the large moment of inertia of the typical camera-lens assembly used for imaging the person's eye, it is impractical to rotate the camera itself. By placing the camera 90 degrees to the side and putting a mirror at 45 degrees in front of the lens to reflect the camera's instantaneous field of view toward the person's eye, high speed eye tracking can be accomplished by rotating the lower-moment-of-inertia mirror assembly rather than rotating the camera-lens assembly.

We began by considering a conventional double gimbal mount for the mirror control assembly. While the moment of inertia for the inner gimbal was sufficiently low to achieve the desired high-speed, high-acceleration response, the inertia of the outer gimbal, which included the mass of the inner motor and frame, was still too high.

Other representative mechanisms for rotating mirrors are disclosed in U.S. Pat. Nos. 4,811,619 to Cutburth; 4,782,474 to Arai et al.; 4,410,233 to Gerhardt et al.; and 4,315,610 to Malueg. In eyegaze tracking technology, U.S. Pat. Nos. 3,804,496; 4,287,410; and 4,373,787, all to Crane et al., describe rotating mirror systems for tracking eye rotations and translations. The later two patents to Crane et al. disclose the use of gimballed mirrors that are pivoted at their centers so as to rotate about their central vertical and horizontal axes. The earlier Crane et al. patent discloses a small, i.e., less than about 2-inch diameter, two dimensionally gimballed mirror. The mirrors for the three Crane et al. patents are disposed in imaging optical systems at real image points and controlled with position-based servomechanisms in which the error signals are derived from motions of Purkinje images on simple quadrant detectors.

The prior mechanisms are generally more complex and expensive than necessary for efficient head tracking. They tend either to have high inertia, limiting their speed and range of response as described above, or to require special location, limiting their use with simple optics. Furthermore, the prior fast response mirrors such as those of Crane et al. are small so as to achieve the 100-Hz responses needed for tracking in-socket eye rotations, and typically use position-based servomechanisms to maintain the image of the eye at a fixed detector location.

SUMMARY

In accordance with the present invention, there is provided an apparatus for tracking an object comprising: a mirror; means for selectively rotating the mirror; means for forming an image of the object reflected from the mirror; means for calculating an angular velocity of the mirror, the angular velocity minimizing blur of the image; and means for controlling the rotating means according to the velocity calculated by the calculating means.

In an another aspect of the invention, there is provided an apparatus for rotating a mirror about two intersecting axes comprising: a support frame; a pivot ball disposed at the intersection of the two axes and attached to the support frame; a frame engaging the pivot ball, the frame being attached to the mirror and having first and second arms, wherein each arm is disposed coaxially with one or the other of the axes and has a tie point at one end thereof; first and second linear actuators for generating linear motions; and first and second rotatable connecting links, the first link engaging the first linear actuator and the tie point of the first arm, the second link engaging the second linear actuator and the tie point of the second arm, wherein linear motions of the first and second linear actuators result in circumferential motions of the tie points.

BRIEF DESCRIPTION OF THE DRAWINGS

The several objects and advantages of the invention will be better understood after a reading of the following detailed description in conjunction with the drawings in which:

FIGS. 7A–7L compare the operations of position and velocity servomechanisms.

DETAILED DESCRIPTION

Figure 1:
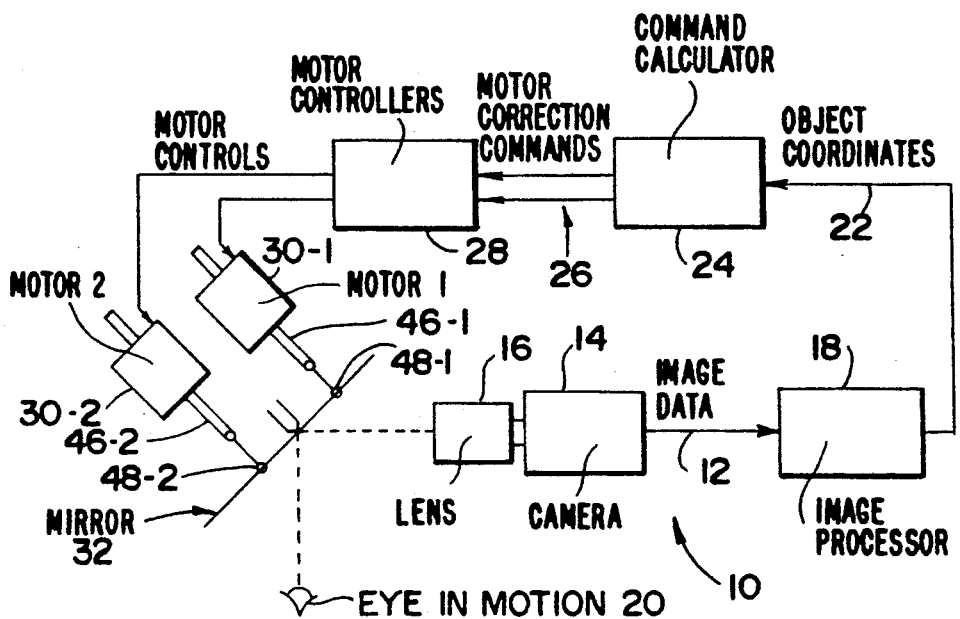
FIG. 1 illustrates an embodiment of the tracker in accordance with the present invention.

Referring now to the Figures in which like parts are identified by like reference numerals throughout, a preferred embodiment of the mirror rotation apparatus 10 is shown in FIG. 1. Video image data 12 from a camera 14 having lens 16 is fed to an image processor 18 which detects an object of interest such as eye 20 or a glint therefrom and determines the object's coordinates 22 within the camera's instantaneous field of view. A command calculator 24 computes motor correction commands 26 for motor controllers 28. The motor correction commands 26 drive motors 30-1, 30-2 to actuate mirror assembly 32 to keep the object at a desired location within the camera field of view. As the mirror moves to correct the tracked object's position within the camera's field of view and a the object itself moves, the apparatus continuously tracks the object as described in more detail below.

Apparatus 10 for use in an eyegaze tracking environment has been constructed using a mirror assembly 32 that is described in more detail below and suitable commercially available components such as a model VDC-3860 CCD video camera 14 made by Sanyo having a model V7514 75-mm f/1.4 lens 12 made by Computar. Image data 12 from camera 14 is provided to a 286-class general purpose digital computer having a 287-class math co-processor and a suitable frame grabber or other video image digitizer. Such a computer and frame grabber are the DESKPRO286 from Compaq and the PC VISION frame grabber board from Imaging Technology, Inc., Woburn, Mass. It will be understood that the frame grabber and computer can be conventionally programmed to implement the functions performed by image processor 18 and command calculator 24, as described further below. Motor correction commands 26 are input to model PCMC-4 stepper motor controller 28 from Advanced Micro Systems, Inc. for driving the model LA23GCKA-200 stepper motors 30-1, 30-2 from Eastern Air Devices. Using these components, apparatus 10 provides +30 degrees tracking range in both pitch and yaw with a frequency response suitable for following even uncontrolled head movements. In addition, when apparatus 10 is combined with means for compensating longitudinal movements, i.e., those along the optic axis of lens 16, such as that disclosed in co-pending U.S. patent application Ser. No. 07/363,716, filed June 9, 1989 now U.S. Pat. No. 4,974,010, for a Focus Control System, incorporated herein by reference, an object or head tracking system is provided that can compensate for movements of ±eight inches side-to-side (yaw), ±six inches up-to-down (pitch) and ±four inches back-and-forth.

Figure 2:
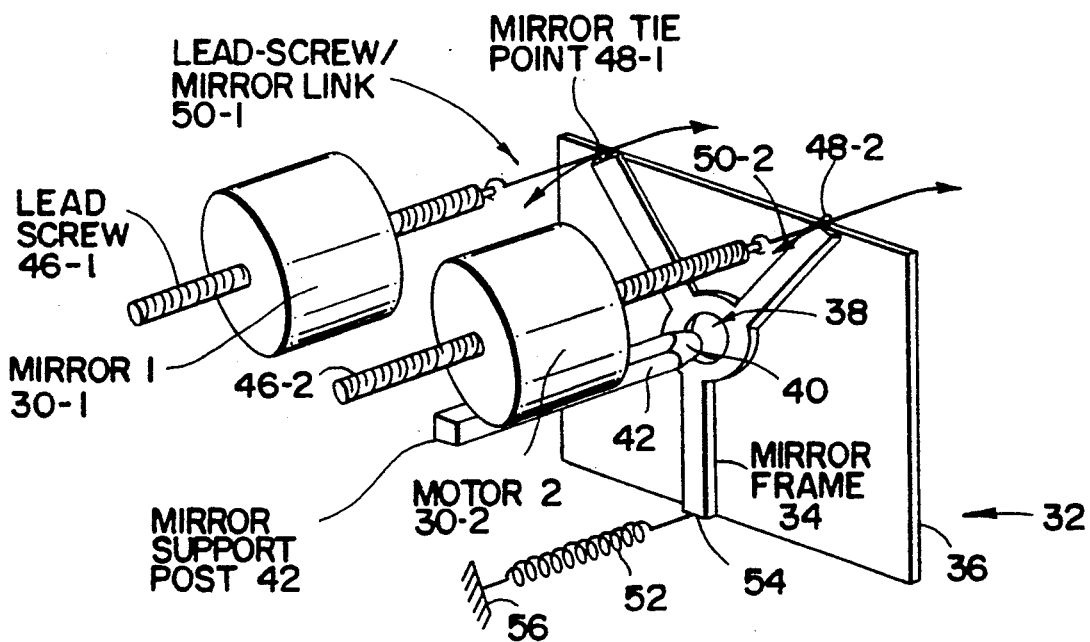
FIG. 2 is a perspective view of a rotatable mirror assembly.

Referring now to FIG. 2 there is shown a preferred embodiment of mirror assembly 32. A Y-shaped frame 34 is suitably attached to the back of mirror 36 to provide attachment mechanisms for the mirror support and rotation controls. A cone-shaped notch 38 at the center of the frame 34 provides a seat for a pivot ball 40 about which the mirror 36 can rotate. It will be appreciated that frame 34 and ball 40 are, in essence, a ball-in-socket joint and thus are fabricated of materials that permit smooth relative movement. Pivot ball 40 can be suitably mounted to support post 42, or post 42 may be given a ball-like end, that in turn is mounted to the mirror assembly chassis 56 (shown only schematically in FIG. 2). In this way, a selected reference point on mirror 36 is securely fixed in the chassis coordinate frame of reference, and mirror 36 can be moved independently in both the pitch and yaw axes. Movement in pitch can be obtained by driving motors 30-1, 30-2 in the same direction, and movements in yaw can be obtained by driving the motors in opposite directions. It will be understood that the orientation of frame 34 with respect to the pitch and yaw directions determines the driving arrangement of the motors.

Stepper motors 30-1, 30-2 and lead screws 46-1, 46-2 are used to effect the mirror pitch and yaw rotations. The motors 30-1, 30-2 are mounted to the mirror assembly chassis such that the lead screws are normal to the mirror plane when in the nominal position and approximately aligned with two mirror control tie points 48-1, 48-2 on mirror frame 34. Tie points 48-1, 48-2 are advantageously disposed on mutually perpendicular arms of frame 34. Because the paths of the mirror tie points are constrained by pivot ball 40 to lie on a spherical surface centered about the pivot ball as mirror 36 moves in pitch and yaw, shown by the double headed arrows, and because lead screws 46-1, 46-2 are constrained to travel in straight lines, rotatable links 50-1, 50-2 connect the ends of lead screws 46-1, 46-2 to mirror tie points 48-1, 48-2. It will be understood that other linear actuator devices are also suitable for generating the motions provided by the motor-lead screw combinations.

Figure 3A:
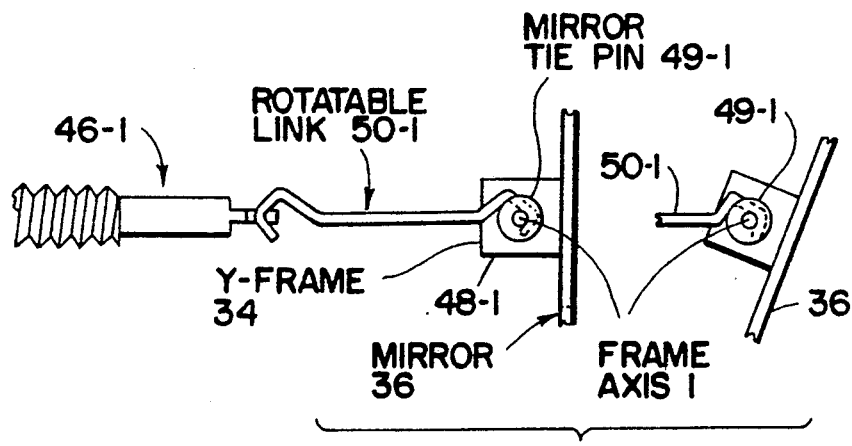
FIGS. 3a and 3b are views showing a connecting link for the rotatable mirror.
Figure 3B:
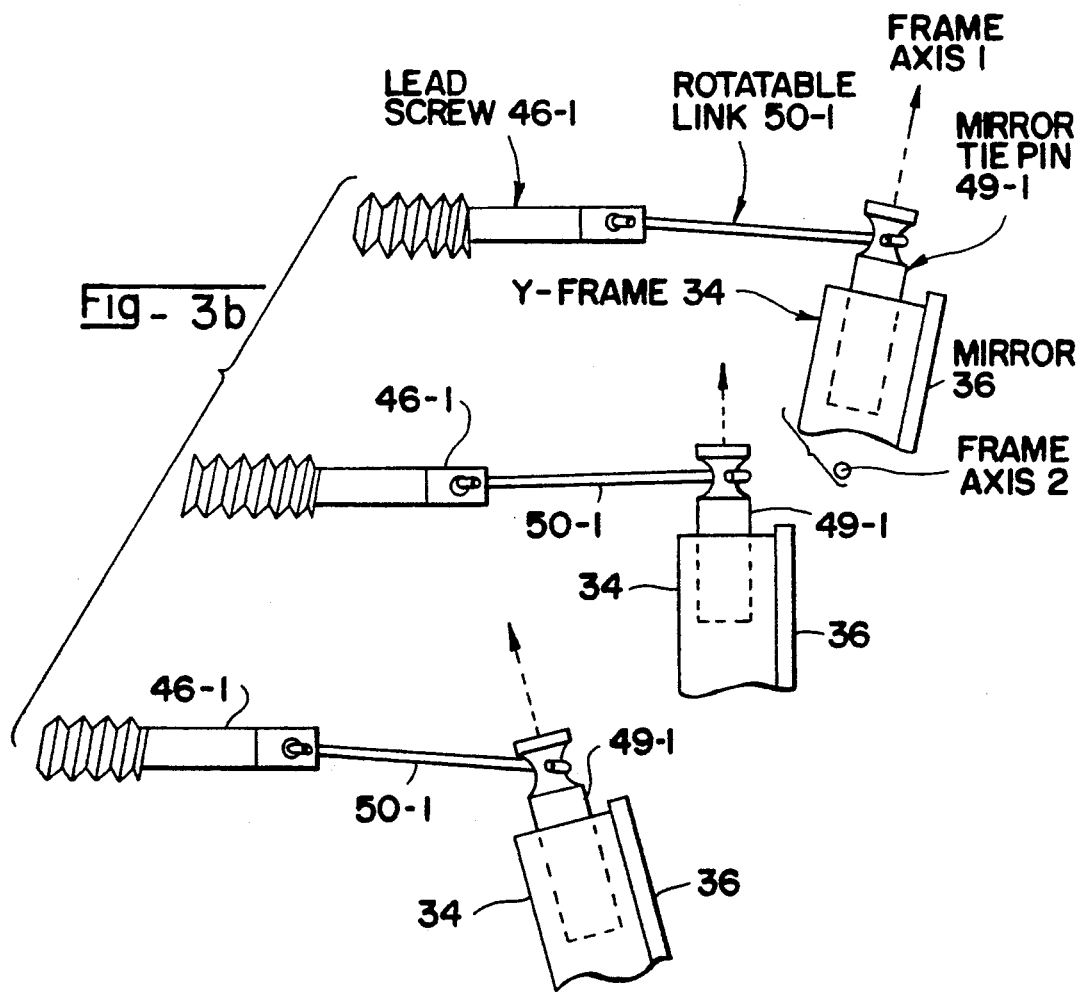

FIGS. 3a and 3b show the arrangement of rotatable connecting link 50-1, lead screw 46-1 and mirror tie point 48-1. The other link 50-2 is arranged in a similar fashion. As described above, the arms of the Y of mirror frame 34 are oriented 90 degrees with respect to each other, and the axes of those arms intersect at the center of the pivot ball. Calling frame axis 1 the axis through tie point 48-1 and frame axis 2 the axis through tie point 48-2, it can be seen from FIG. 1 that translation of lead screw 46-1 causes mirror rotation about frame axis 2, and translation of lead screw 46-2 causes mirror rotation about frame axis 1. As described above, rotatable links 50-1, 50-2 connect the lead screws to the mirror tie points in such a way as to allow the linear translation of the lead screw to result in a circumferential translation of the mirror tie points.

FIGS. 3a and 3b show end and side views of several positions of link 50-1 and its connections to lead screw 46-1 and the mirror tie point 48-1. As illustrated in FIG. 3a, the link is a hardened steel wire-form part with hooks on each end. The end of the lead screw is machined flat on each side and a hole is drilled through it to accept the hook on one end of the link. It will be understood that the lead screw does not rotate about its translation axis. As seen more clearly in FIG. 3b, mirror tie point 48-1 is constructed from a rod, called a tie pin 49-1, which is fitted into the end of the Y frame arm coaxially with the arm axis. Tie pin 49-1 is machined with a circumferential groove in which the hook on the other end of link 50-1 is retained.

The shapes of the hooks on the rotatable link, the hole in the lead screw, and the groove in the tie pin are designed to accommodate the rotating motions that the link experiences throughout all ranges of operation. The hooks must remain stably connected; material wear should be minimized; and smoothness of operation must be maintained. The bent wire-form shape of the link is chosen (rather than a stamping from sheet metal for example) to achieve the compound curvatures required to mate the contacting surfaces most evenly and thus minimize wear. The hole through the lead screw is chamfered on each side to match the curvatures of the hole to the curvatures of the hook. The inner radius of the groove in the tie pin matches the radius of the link wire.

As can be seen in FIG. 3a, when the mirror rotates about frame axis 1, tie pin 49-1 rotates within the hook at the end of link 50-1. The groove in the tie pin is circumferential to accommodate this rotation. As can be seen in FIG. 3b, link 50-1 rotates up and down as the lead screw translates forward and back (illustrated by the three views in FIG. 3b). The angles of the groove in the tie pin are accordingly selected to allow the link to rotate with respect to the tie pin but also to maintain a firm connection between the link and the pin when the mirror is at its extreme angles.

Figure 4:
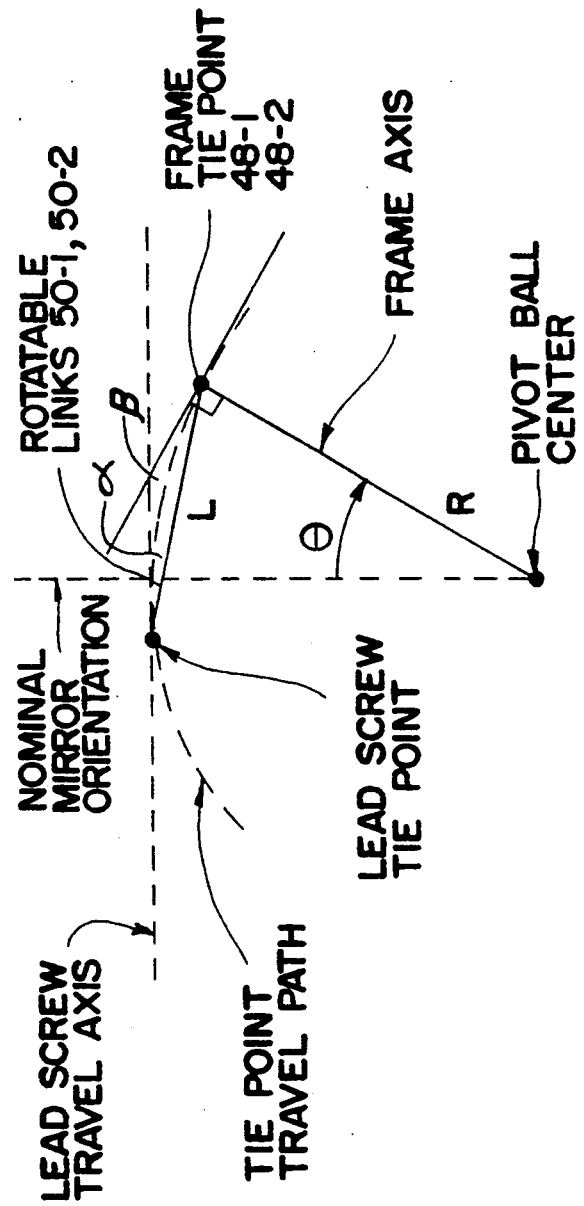
FIG. 4 shows a geometry of a portion of the rotatable mirror assembly.

FIG. 4 shows the geometry of the lead screw travel axis, the connecting link and the Y frame as a function of the mirror angle $\theta$, where $\theta$ is measured from a nominal mirror orientation normal to the lead screw travel axis. From this geometry, it can be determined that the angle $\alpha$ between the lead screw travel axis and the connecting link is:

$$\alpha = \arcsin\{R(1-\cos\theta)/L\}$$

and the angle $\beta$ between the connecting link and the normal to the tie pin is:

$$\beta = \theta - \alpha$$

where R is the radius from the center of the pivot ball to the frame tie point, and L is the connecting link length. It can be noted that angle $\alpha$ is positive for both positive and negative mirror angles $\theta$.

The optimum link length L depends on the maximum amount of angular travel $\theta$ required by the mirror. Longer links result in less rotation of $\alpha$ and $\beta$ and therefore allow greater angular travel of the mirror. On the other hand, longer links also result in a larger size of the overall mirror control assembly. In an eye tracking application where it is desired for the camera to track an eye over an angular range of 60 degrees, the mirror must have a total travel of 30 degrees. (Because both the angle of incidence and reflection change as the mirror rotates, the reflected camera axis rotates 2 degrees for every 1 degree of mirror rotation, and the total mirror travel is half the travel of the reflected camera axis.) To get the total 30 degree mirror travel, the minimum and maximum values of $\theta$ are $-15$ degrees and $+15$ degrees. The angle maximum angle $\theta$ can be kept to less than 19 degrees if L is set to about about half of the tie point radius R.

In the eye-tracking application it is necessary to obtain high resolution control of the mirror angles to minimize image blur when tracking an eye that is in motion. Any hysteresis or looseness in the mirror assembly results in decreased precision and increased blur in the image. As shown in FIG. 2, a suitable method for eliminating hysteresis is to attach a spring 52, between the assembly chassis and a tie point 54 on mirror frame 34. With mirror frame 34 acting as a lever rotating on pivot ball 40 and mirror links 50-1, 50-2 constraining the circumferential travel of the angle-control tie points about pivot ball 40, spring 52 holds the mirror stably seated on the pivot ball 40, maintains dimensional stability of the mirror links 50-1, 50-2 between the ends of lead screws 46-1, 46-2 and mirror tie points 48-1, 48-2, and eliminates hysteresis in the lead-screws' travel through the drive nuts in motors 30-1, 30-2.

From FIG. 2, it can be seen that the rotating portion of the mirror control assembly 32 has a very low moment of inertia. The inertia is due only to the mirror 36, the mirror frame 34, the mirror links 50-1, 50-2 and the lead screws 46-1, 46-2. Compared to a double gimballed frame, the Y-frame 34 is lighter and significantly simpler, and the masses of both motors 30-1, 30-2 are excluded from any driven load. The low moment of inertia of mirror assembly 32 allows smooth, high-speed, high-acceleration tracking with smaller, lighter and less expensive motors. Furthermore, the moment of inertia that each motor must drive is identical, so the mirror responds with equal dynamics in both pitch and yaw axes.

Figure 5:
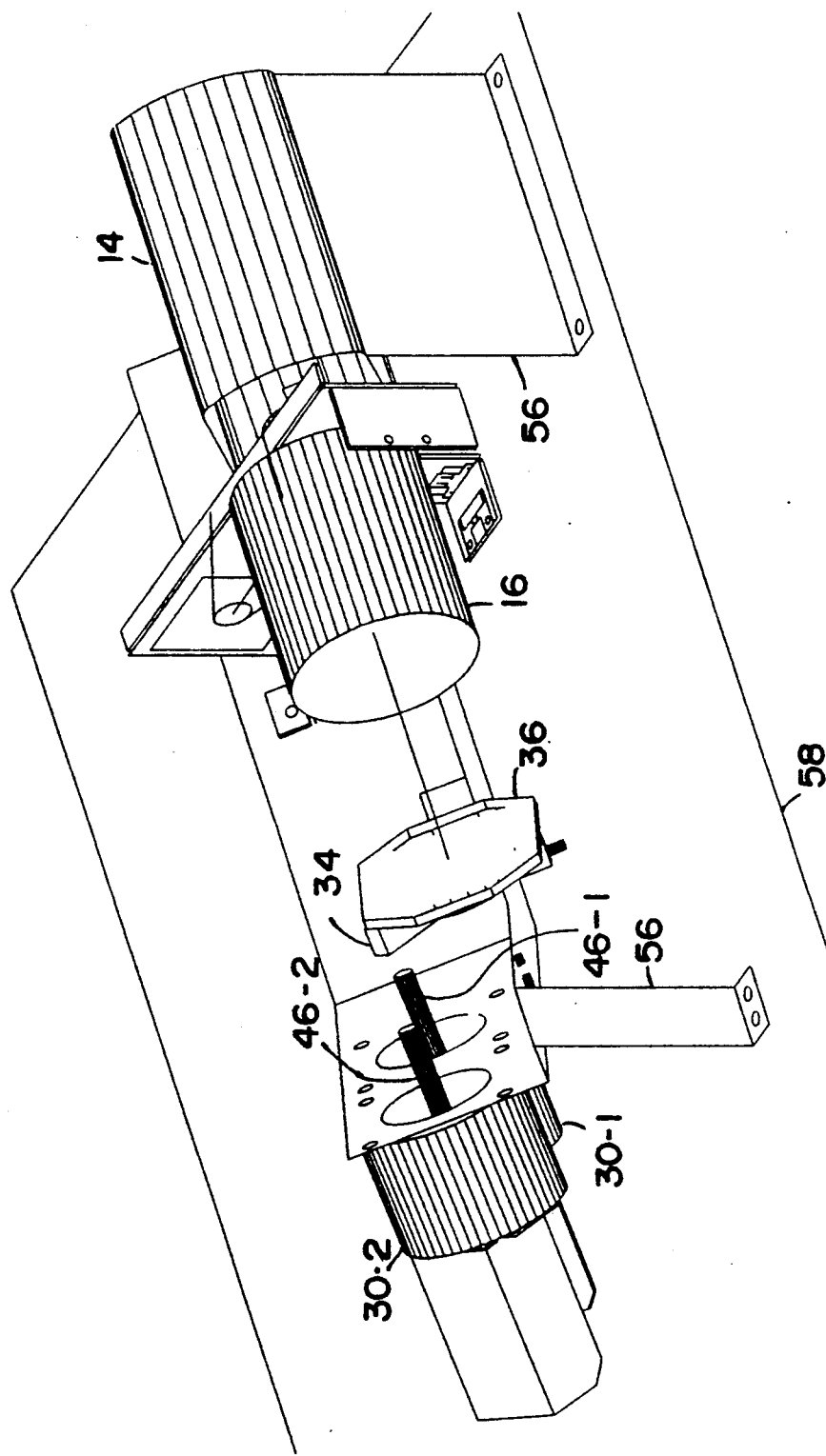
FIG. 5 shows a configuration of a portion of the tracker.

FIG. 5 shows a configuration of a portion of mirror rotation apparatus 10 including mirror assembly 32 suitable for use in eyegaze tracking. Motors 30-1, 30-2 and camera 14 are shown supported by chassis 56 which is disposed on a suitable surface 58. The connecting links 50-1, 50-2, spring 52 and support post 42 are not shown in FIG. 5. The chassis 56 is angled with respect to surface 58 because the tracking apparatus is typically disposed below the person's eye level in the eyegaze tracking application.

Referring again to FIG. 1, a suitable image processor 18 comprises a frame grabber such as the PC VISION FRAME GRABBER board made by Imaging Technology, Inc., Woburn, Mass., a general purpose digital computer such as the DESKPRO-286 computer made by Compaq with a 287 math coprocessor, and a suitable image processing program. The object-detection (i.e., the determination of the existence and approximate location of the object in the field of view) and object-location (i.e., the determination of the precise location coordinates of the object in the field of view) operations of the image processing program depend on the type of object being tracked. In an eye tracking application, the direct reflection of a light source from the cornea of the eye can be detected, and that reflection can be maintained at the center of the field of view or video image. A suitable image processing program executed by the computer typically detects the corneal reflection by looking for light-level intensities that exceed a certain brightness threshold. The precise coordinates of the reflection image are advantageously computed by calculating the center of mass of local pixel intensities that exceed the brightness threshold as set forth in co-pending U.S. patent application Ser. No. 07/363,873 for a Method and Apparatus for Locating Image Features, now U.S. Pat. No. 4,974,010 incorporated herein by reference.

Based upon the magnification factor of the camera lens and upon the dimensions of the camera sensor's grid of picture elements (pixels), command calculator 24 computes an angular correction of the camera's effective pointing direction that will move the corneal reflection to the center of the camera field of view.

Figure 6:
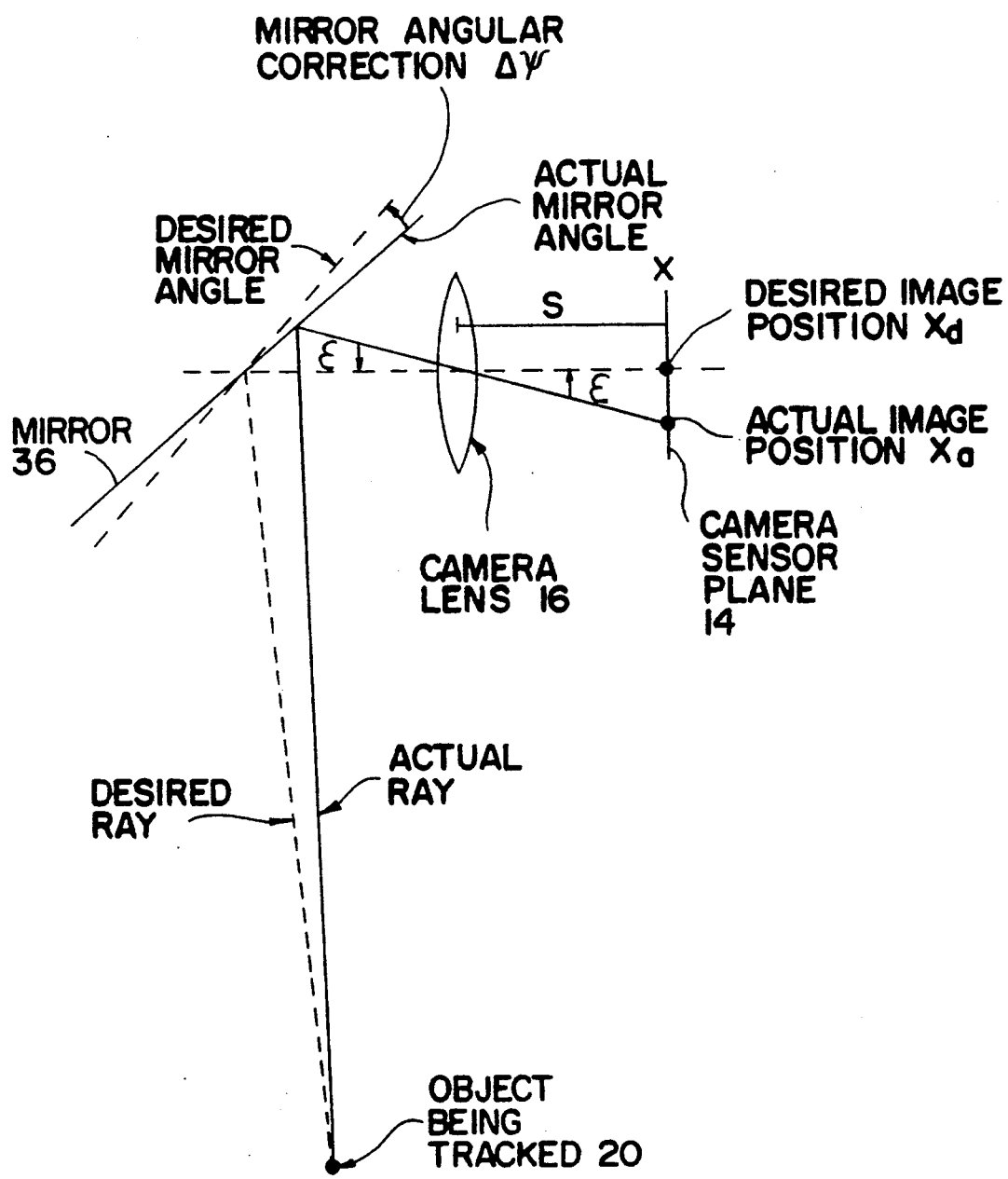
FIG. 6 shows ray trace geometry for a tracked object.

FIG. 6 shows ray trace geometry of an object 20 being tracked by camera 14 which is viewing the object through mirror 36. The solid ray lines and the solid mirror line indicate the mirror tracking condition when the image being tracked is not at its desired position $x_d$ on the camera's sensor plane. The actual image position is denoted $x_a$. The dashed ray lines and dashed mirror line in FIG. 6 indicate the desired mirror tracking condition. From the point of view of the image processor, the measured tracking error $e_x$ with respect to the camera sensor plane is:

$$e_x = x_d - x_a$$

The angular error $\epsilon$ of the object ray is:

$$\epsilon = \arctan(e_x/s)$$

where s is the distance from the camera lens plane to the camera sensor plane. Assuming that the distance from the lens 16 to mirror 36 is small with respect to the distance from the camera to the object being tracked, the angular mirror correction required to shift the actual object ray to the desired object ray is half the angular error $\epsilon$, i.e.:

$$\Delta\psi = \epsilon/2$$

since both the angle of incidence and the angle of reflection change as the mirror rotates, i.e., the reflected object ray rotates 2 degrees for every 1 degree of mirror rotation. Solving the above two equations yields the mirror angular correction $\Delta\psi$ as a function of the measured positional tracking error $e_x$:

$$\Delta\psi = \arctan(e_x/s)/2$$

Similarly, the correction for the other orthogonal camera angle is:

$$\Delta\theta = \arctan(e_y/s)/2$$

As described above, linear translations of lead screws 46-1, 46-2 result in angular rotations of mirror 36. It will be appreciated that the mathematical equations relating the magnitudes of lead screw translations to the magnitude of mirror angular rotation can be determined in a straightforward way from the geometric configuration and dimensions of the mirror control assembly 32. In the embodiment shown in FIG. 2, synchronous motions of lead screws 46-1, 46-2 result in pitch motions of the mirror, and differential motions result in mirror yaw motions. The command calculator 24 computes the linear translations required of the lead screws to achieve the desired mirror rotations; accordingly, the command calculator 24 can be realized by conventionally programming the same digital computer used for image processor 18 to implement the equations relating lead screw translation to mirror rotation. In this way, portions of apparatus 10 embody a servomechanism for positioning mirror 36.

As described above, motor controllers 28 drive motors 30-1, 30-2 such that lead screws 46-1, 46-2 follow commands 26 from command calculator 24. It is important, however, that overall operation of the apparatus 10 be rapid, smooth and stable. Thus, it will be appreciated that motor controllers 28 may include appropriate signal gains and phase compensation required to obtain the desired overall closed-loop performance. Conventional Laplace or state-variable analysis techniques can be used to synthesize appropriate stability compensation for the servomechanism.

In many prior photographic tracking applications, the primary objective of the control system was to keep the image of the object being tracked precisely located within the camera frame of reference. For eyegaze tracking, we have found that as long as the image is clear and its position can therefore be precisely calculated, controlling the position of the object's image is not important. As long as the image of the tracked eye remains within the camera's field of view, position offset errors have no adverse effect on the image's quality, so precise image position control becomes a secondary objective. Indeed, it is desirable to trade increased image positional tracking errors for reduced image motion and increased image clarity.

One way to reduce the net motion of an object's image while the object is accelerating or decelerating is to use a velocity control strategy for the servomechanism rather than a position control strategy. In the velocity control strategy, motor correction commands 26 are issued in terms of mirror angular rates rather than mirror angular positions.

FIGS. 7A-7L show comparative dynamic responses of the mirror tracking servo when using position and rate control strategies. To highlight the differences in the responses, the tracked object is assumed to experience a step velocity change at time $t=0$ (see FIGS. 7A-B, 7G-H). In the position control case, the position tracking error initially rises as the object begins to move (see FIG. 7D), and the controller accelerates the mirror to stop the error growth (see FIG. 7C). So that the controller can eliminate the position error, the acceleration continues until the mirror velocity exceeds the object velocity, and as the mirror position catches up with the object and the error begins to drop back to zero, the controller then decelerates the mirror until its speed and position match the tracked object (see FIG. 7E). In the velocity control case, the position tracking error also initially rises as the object begins to move (see FIG. 7J), and the controller accelerates the mirror into motion (see FIG. 7I). Compared to the position control strategy, the mirror velocity in the velocity control strategy never exceeds the object velocity so there is no subsequent deceleration (see FIG. 7K). In the steady-state, a constant position tracking error remains. It will be appreciated that the general principles of control systems such as position and velocity servos are set forth in a number of texts, such as B.C. Kuo, "Automatic Control Systems," 2d ed., Prentice-Hall, Englewood Cliffs, N.J. (1967).

As shown in FIGS. 7F and 7L, the blurriness of the image at any time is directly proportional to the magnitude of the speed of the image within the camera frame of reference at that time. In the rate control case in accordance with the present invention, the net image motion is greatly reduced in comparison to the position control case. With position control, excess image motion and blur results from the mirror acceleration required to get the mirror velocity temporarily to exceed the object velocity and the deceleration then required to get the mirror velocity back down to the object velocity.

The present invention has been described in connection with embodiments and illustrations which are to be considered in all senses to be illustrative, not restrictive. Those of ordinary skill in the art will recognize modifications which do not depart from the spirit and scope of the invention which is to be limited solely by the following claims.

What is claimed is:

1. An apparatus for rotating a mirror about two intersecting axes comprising:
    a support frame;
    a pivot ball disposed at the intersection of the two axes and attached to the support frame;

a frame engaging the pivot ball, the frame being attached to the mirror and having first and second arms, wherein each arm is disposed coaxially with one or the other of the axes and has a tie point at one end thereof;

first and second linear actuators for generating linear motions;

first and second rotatable connecting links, the first link engaging the first linear actuator and the tie point of the first arm, the second link engaging the second linear actuator and the tie point of the second arm, wherein linear motions of the first and second linear actuators result in circumferential motions of the tie points; and a bias means, wherein the bias means is attached at one of its ends to the support frame and at its other end to the frame attached to the mirror, the bias means opposing linear motions of the linear actuators.

2. The apparatus of claim 1, wherein the bias means is a spring.

3. An apparatus for tracking an eye comprising:

a mirror;

means for selectively rotating the mirror;

means for forming an image of the eye reflected from the mirror, said means for forming an image having a sensor and a field of view wider than the image of the eye;

means for locating the position of the eye within the field of view;

means for calculating the angular error in tracking the eye by determining the distance in the plane of the sensor between the position of the image of the eye and a desired position within the field of view of the means for forming the image;

means for calculating an angular velocity command for the mirror to correspond to the angular tracking error of the eye, thus minimizing blur of the image formed; and means for controlling the rotating means according to the angular velocity command.

4. The apparatus of claim 3, wherein the means for calculating the position of the eye includes means for locating the image of the pupil of the eye.

5. The apparatus of claim 3, wherein the means for calculating the position of the eye includes means for locating the image of the reflection of light off the cornea of the eye.

6. The apparatus of claim 3, wherein the rotating means rotates the mirror independently in two axes.

7. The apparatus of claim 3, wherein the means for forming an image is a video camera.

8. A method for tracking an eye comprising:

positioning a mirror to reflect the eye to a means for forming an image of the eye, said means for forming an image having a sensor and a field of view wider than the image of the eye;

forming an image of the eye from the reflection of the eye in the mirror;

locating the position of the eye within the field of view;

calculating the angular error in tracking the eye from the distance in the plane of the sensor between the position of the image of the eye and a desired position within the field of view of the means for forming the image;

calculating an angular velocity command for the mirror corresponding to the angular tracking error of the eye being tracked to minimize the blur of the image; and controlling the angular velocity of the mirror according to the calculated angular velocity command.

9. The method of claim 8, wherein locating the position of the eye includes locating the image of the pupil of the eye.

10. The method of claim 8, wherein locating the position of the eye includes locating the image of the reflection of light off the cornea of the eye.

11. The method of claim 8, wherein the means for forming an image is a video camera.

* * * * *